(12) United States Patent
Pinchot

(10) Patent No.: US 12,268,513 B2
(45) Date of Patent: Apr. 8, 2025

(54) MONITORING OF PATIENTS FOR SEPSIS BASED ON RADIOISOTOPE LEVEL

(71) Applicant: Roy Pinchot, Netanya (IL)

(72) Inventor: Roy Pinchot, Netanya (IL)

( * ) Notice: Subject to any disclaimer, the term of this patent is extended or adjusted under 35 U.S.C. 154(b) by 66 days.

(21) Appl. No.: 18/244,484

(22) Filed: Sep. 11, 2023

(65) Prior Publication Data
US 2025/0082259 A1    Mar. 13, 2025

(51) Int. Cl.
*A61B 5/083* (2006.01)
*A61B 5/00* (2006.01)
*A61B 5/145* (2006.01)
*G16H 20/17* (2018.01)
*G16H 20/40* (2018.01)

(52) U.S. Cl.
CPC ............ *A61B 5/412* (2013.01); *A61B 5/0836* (2013.01); *A61B 5/14546* (2013.01); *A61B 5/746* (2013.01); *G16H 20/17* (2018.01); *G16H 20/40* (2018.01)

(58) Field of Classification Search
CPC ... A61B 5/412; A61B 5/0836; A61B 5/14546; A61B 5/746
See application file for complete search history.

(56) References Cited

U.S. PATENT DOCUMENTS

| | | | | |
|---|---|---|---|---|
| 8,435,187 B2 * | 5/2013 | Assadi-Porter | ........ | A61B 5/082 600/532 |
| 10,139,392 B2 * | 11/2018 | Kääriäinen | ............ | A61B 5/082 |
| 10,165,965 B1 * | 1/2019 | Javitt | ................. | A61B 5/082 |
| 10,694,993 B2 * | 6/2020 | Butz | ................. | A61B 5/082 |
| 2012/0220845 A1 * | 8/2012 | Campbell | .............. | A61B 5/412 600/364 |

OTHER PUBLICATIONS

Song J. et al., "Sepsis: Recoginition and Treatement", CME Acute Medicine; Clinical Medicine 2012, vol. 12, No. 3:276-80; Royal College of Physicians, 2012.

* cited by examiner

*Primary Examiner* — Eric F Winakur
(74) *Attorney, Agent, or Firm* — Panitch Schwarze Belisario & Nadel LLP

(57) ABSTRACT

A method, system, and computer program product for monitoring sepsis in a subject. A device may monitor expired air from the subject who has been administered a bicarbonate salt comprising a carbon-13 isotope. The device may measure a ratio of carbon dioxide comprising the carbon-13 isotope ($^{13}CO_2$) to carbon dioxide comprising a carbon-12 isotope ($^{12}CO_2$) in the monitored expired air and may determine a level of sepsis in the subject based on the ratio, where a lower ratio of $^{13}CO_2$ to $^{12}CO_2$ indicates an increased level of sepsis. The device may display an indication of the level of sepsis in the subject.

17 Claims, 8 Drawing Sheets

MONITORING OF PATIENTS FOR SEPSIS BASED ON RADIOISOTOPE LEVEL

FIELD OF THE DISCLOSURE

The present disclosure relates generally to a method, system, and computer program product for monitoring of subjects for sepsis, and more particularly to monitoring of patients for sepsis based on radioisotope level, e.g., a radioactive carbon compound.

BACKGROUND OF THE DISCLOSURE

Sepsis is a potentially life-threatening condition that occurs when the body's response to an infection damages its own tissues. When the infection-fighting processes turn on the body, they cause organs to function poorly and abnormally, which may progress to septic shock. Septic shock is a dramatic drop in blood pressure that results in high abnormality in how cells function and produce energy, which can lead to severe organ problems and death. Progression to septic shock increases the risk of death and thus patient monitoring is vital in detecting/reducing the risk of sepsis in patients. A recent study found 35% of in-hospital deaths in the United States are caused by sepsis, making it a leading cause of in-hospital death. The cost of sepsis management in U.S. hospitals ranks highest among admissions for all disease states (1.7 million patients annually) and indeed the costs for sepsis are currently more than twice those of other conditions and continue to grow at three times the rate of other admissions. A diagnosis of sepsis leads to increased mortality and an increase in a patient's length of stay (LOS) in the hospital. The average LOS for sepsis patients in U.S. hospitals is approximately 75% greater than for most other conditions and LOS is reported to dramatically increase with sepsis severity, e.g., 4.5 days for sepsis, 6.5 days for severe sepsis, and 16.5 days for septic shock. Therefore, early recognition and treatment of sepsis are linked to improved patient outcomes, containment of a major hospital cost problem, and a potential solution to hospital over-crowding by freeing many more beds for patients needing care. "It is one of the leading causes of death in the United States, on par with cancer and heart disease," says Yale Medicine emergency physician John Sather, MD. One way to detect sepsis is through the measurement of lactate in a patient's bloodstream, e.g., serum lactate. Having too much lactic acid in the bloodstream, e.g., serum lactate, means that the cells are deficient in oxygen—not using oxygen properly. Thus, lactate measurement/monitoring is a useful method of determining sepsis prognosis. It has been found that patients with a bloodstream serum lactate level greater than 4 mmol/L have a mortality rate of 40% and those with a bloodstream serum lactate level of less than 2 mmol/L have a mortality rate of 15%. Current methods and techniques for measuring serum lactate are performed by physically/invasively puncturing the body to draw blood for the monitoring of Arterial Blood Gases (ABGs). However, because of its invasive nature, such ABG monitoring is only done periodically, and therefore sepsis, in a high percentage of current cases, is not detected until it has progressed significantly and may be tragically irreversible. Thus, there is a need for a novel, non-invasive solution for monitoring a subject on an on-going basis to enable earlier detection of sepsis.

SUMMARY OF THE DISCLOSURE

The present disclosure provides a description of exemplary methods, systems, and computer program products that may be used to monitor subjects for sepsis based on radioisotope level in accordance with various aspects of the present disclosure.

This novel method for monitoring sepsis may include monitoring expired air from the subject, wherein the subject has been administered a bicarbonate salt comprising a carbon-13 isotope; measuring a ratio of carbon dioxide comprising the carbon-13 isotope ($^{13}CO_2$) to the naturally occurring carbon dioxide comprising a carbon-12 isotope ($^{12}CO_2$) in the monitored expired air, wherein the ratio correlates to a bloodstream level of lactic acid in the subject; determining a level of sepsis in the subject based on the ratio, wherein a lower ratio of $^{13}CO_2$ to $^{12}CO_2$ indicates an increased level of sepsis; and displaying an indication of the level of sepsis in the subject. The method may include generating an alert when the ratio of $^{13}CO_2$ to $^{12}CO_2$ in the monitored expired air exceeds a defined threshold. The method may also include adjusting treatment of the subject when the ratio of $^{13}CO_2$ to $^{12}CO_2$ in the monitored expired air exceeds a defined threshold.

A device for monitoring sepsis in a subject may include a respiratory monitor configured to monitor expired air from a subject, wherein the subject has been administered a bicarbonate salt comprising a carbon-13 isotope. The device may include a processor configured to measure a ratio of carbon dioxide comprising the carbon-13 isotope ($^{13}CO_2$) to a carbon dioxide comprising a carbon-12 isotope ($^{12}CO_2$) in the monitored expired air, wherein the ratio correlates to a bloodstream level of lactic acid in the subject and determine a level of sepsis in the subject based on the ratio, wherein a lower ratio of $^{13}CO_2$ to $^{12}CO_2$ indicates an increased level of sepsis. The device may further include a display configured to display an indication of the level of sepsis in the subject.

A computer program product for monitoring sepsis in a subject may include a computer-readable storage medium having program instructions embodied therewith, the program instructions executable by a computer to cause the computer to perform a method that may include: receiving a carbon-13 isotope ($^{13}CO_2$) measurement and a carbon-12 isotope ($^{12}CO_2$) measurement in expired air from a subject, wherein the subject has been administered a bicarbonate salt comprising the carbon-13 isotope; determining a ratio of $^{13}CO_2$ to $^{12}CO_2$ based on the $^{13}CO_2$ measurement and the $^{12}CO_2$ measurement, wherein the ratio correlates to a bloodstream level of lactic acid in the subject; determining a level of sepsis in the subject based on the ratio, wherein a lower ratio of $^{13}CO_2$ to $^{12}CO_2$ indicates an increased level of sepsis; and displaying an indication of the level of sepsis in the subject.

BRIEF DESCRIPTION OF THE DRAWINGS

The scope of the present disclosure is best understood from the following detailed description of various aspects of the present disclosure when read in conjunction with the accompanying drawings. Included in the drawings are the following figures.

Further areas of applicability of the present disclosure will become apparent from the detailed description provided hereinafter. It should be understood that the detailed description of various aspects of the disclosure are intended for illustration purposes only and are, therefore, not intended to necessarily limit the scope of the disclosure.

DETAILED DESCRIPTION

The present disclosure provides a novel technical solution for monitoring sepsis in a subject. Particularly, various aspects of the methods, devices, and computer program products provided for herein may enable a technique of continuous and non-invasive monitoring of sepsis in a subject based on a radioisotope level, e.g., a radioactive carbon compound, measured in the subject's expired breath. Current methods and techniques such as ABGs are not continuous processes, and thus they may not detect sepsis until it has progressed significantly and perhaps irreversibly. Various aspects of the present disclosure may provide a novel way for monitoring a subject for sepsis utilizing the subject's natural body process of neutralizing excessive lactic acid. Particularly, various aspects of the present disclosure may provide a novel way for monitoring a subject for sepsis by administering a bicarbonate salt comprising a carbon-13 isotope to a subject, monitoring the expired breath from the subject, and measuring a ratio of carbon dioxide comprising the carbon-13 isotope ($^{13}CO_2$) to carbon dioxide comprising a carbon-12 isotope ($^{12}CO_2$) in the monitored expired air, wherein the ratio correlates to a bloodstream level of lactic acid in the subject. For example, a carbon-13 isotope of bicarbonate may be added into a subject's intravenous (IV) drip, which is then metabolized by the subject and mixed with the subject's natural bicarbonate lactate-buffering isotope carbon-12. A lower ratio of metabolized carbon-13 relative to carbon-12 may indicate the over-production of lactic acid, which is a warning sign that the body is actively fighting a dangerous rising level of sepsis in the subject. Various aspects of the present disclosure may include monitoring the breath exhaled by the subject through a machine process that compares the ratio of carbon-13 relative to carbon-12 in the expired breath and calculates a level of sepsis based on the ratio, the ratio indicating a level of lactic acid production in the subject, e.g., the lower the ratio of carbon-13 relative to carbon-12, the higher the lactic acid production in the subject, and thus the higher level of sepsis present in the subject. Therefore, various aspects of the present disclosure may enable earlier detection of sepsis in a subject, which may result in earlier treatment and subject stabilization, which may result in improved subject outcomes.

Environment for Generating Graphics for Monitoring Sepsis in a Subject

Figure 1:
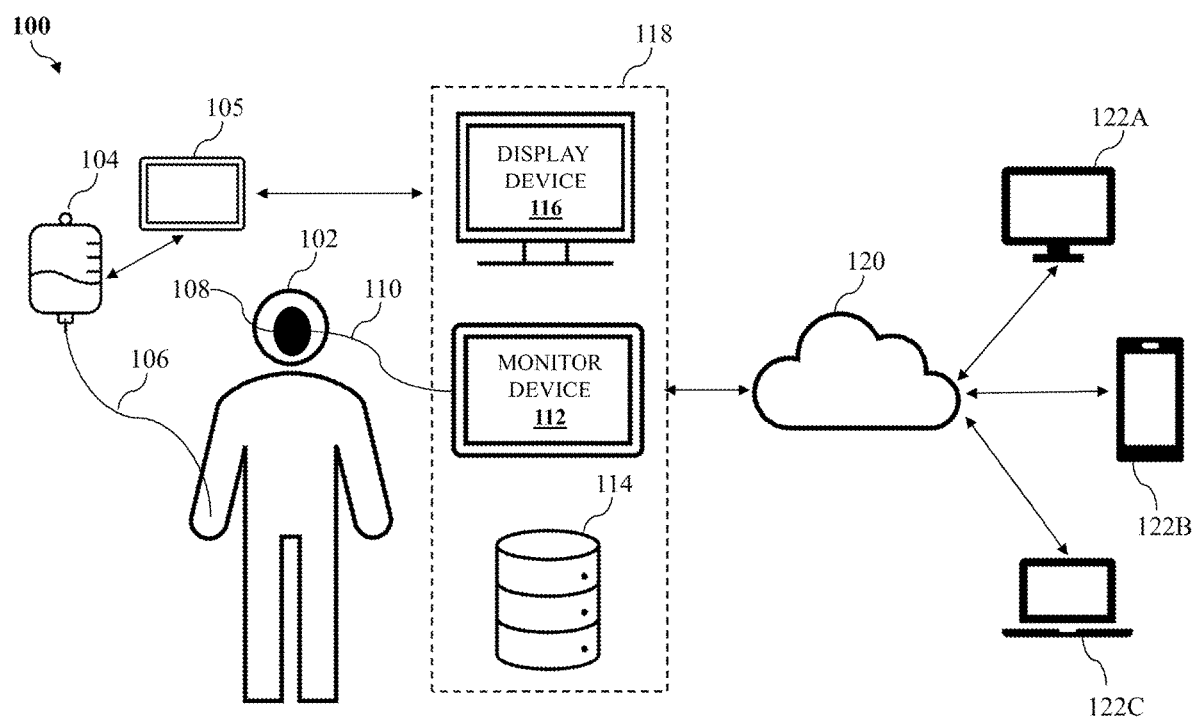
FIG. 1 is a block diagram illustrating a high-level environment for monitoring sepsis in a subject in accordance with aspects of the present disclosure.

FIG. 1 illustrates an example of an environment 100 for monitoring sepsis in a subject. The environment 100 may include a patient 102, an intravenous (IV) drip 104, a respiration device 108, a monitor device 112, a datastore 114, a display 116, and user devices 122.

The environment 100 may be part of any facility in which subjects may be monitored for sepsis. For example, the environment 100 may be, but is not limited to, a hospital, a medical clinic, a doctor's office, a veterinary hospital, a veterinarian's office, or any other suitable medical facility, etc. As a further example, the environment 100 may be an operating room or an intensive care unit (ICU) in a medical facility where a medical professional may need to measure a subject's bloodstream lactic acid levels, e.g., during cardiac surgery, during trauma surgery, during exploratory surgery, assessing vascular health, during post-operative patient assessments, etc.

The subject 102 may be any animal capable of metabolizing a bicarbonate salt comprising a carbon-13 isotope, generating lactic acid, and suffering from sepsis. For example, the subject 102 may be, but is not limited to, a mammal, a bird, a reptile, an amphibian, a reptile, or a fish, etc. According to an aspect of the present disclosure, the subject 102 may be a human subject. For example, the subject 102 may be a human who has been admitted to a medical facility or any other suitable facility in which the subject 102 is to be monitored for possible sepsis symptoms.

The subject 102 may be connected to an intravenous (IV) drip 104 via connection 106. Any known or suitable IV drip may be used as the IV drip 104. The IV drip 104 may be used to administer one or more fluids directly into the bloodstream of the subject 102. The connection 106 may be any suitable connection used as part of the IV drip 104 such as, but not limited to, IV tubing, etc. The IV drip 104 may include and/or be connected to (including, as a non-limiting example, being directed through) an IV monitoring device 105. The IV monitoring device 105 may be any device capable of interacting with the IV drip 104 to control and/or monitor the administration of fluids, medications, and/or nutrients, etc. to the subject 102 such as, but not limited to, an infusion pump or any other suitable device. The IV monitoring device 105 may be connected to the IV drip 104 and/or the monitor device 112 via a hardwired or wireless connection. For example, IV monitoring device 105 may be connected to the IV drip 104 and/or the monitor device 112 by a hard-wired communications connection such as, but not limited to, a universal serial bus (USB) cable, a FireWire cable, an Ethernet connection, or any other suitable wired communications connection. In some embodiments, the IV monitoring device 105 may be connected to the IV drip 104 and/or the monitor device 112 by a wireless communications connection such as, but not limited to, a WiFi connection, a Bluetooth connection, a radio-frequency (RF) connection, a near-field communication (NFC) connection, a satellite connection, or any suitable wireless connection for transmitting data between the respiratory device 108 and the monitor device 112. In environment 100, the IV monitoring device 105 may control an amount, e.g., a dosage or flow rate, etc., of fluid being administered to the subject 102. The IV monitoring device may receive input from a user and/or another computing device, e.g., the monitor 112, to control and/or monitor the IV drip 104. For example, a medical professional may input a dosage amount of a fluid to be administered to the subject 102 via the IV drip 104 and the IV monitoring device 105 may control the administration of the fluid to the subject 102. As another example, the monitor device 112 may generate instructions and transmit those instructions to the IV monitoring device 105 directing the IV monitoring device 105 to begin and/or adjust the administration of fluids to the subject 102. In the environment 100, the IV drip 104 and/or the IV monitoring device 105 may be used to administer a bicarbonate salt, such as, but not limited to, sodium bicarbonate ($NaHCO_3$) to the subject 102. The sodium bicarbonate may comprise a carbon-13 isotope. While an IV drip 104 and the IV monitoring device 105 are illustrated and discussed throughout the disclosure, it can be appreciated that any suitable means of administering a bicarbonate salt, e.g., sodium bicarbonate comprising a carbon-13 isotope, may be used such as, but not limited to, a peripheral IV line, a peripherally inserted central-line catheter (PICC), a central venous catheter (CVC), a mid-line catheter, a pill administered orally, a fluid administered orally, or a subcutaneous injection, etc.

The subject 102 may be connected to a respiratory device 108. The respiratory device 108 may be any device capable of capturing the exhaled breath of the subject 102 for analysis. The respiratory device 108 may be connected to the monitor device 112 via the connection 110. The connection 110 may be a hard connection such as, but not limited to, tubing for transporting air to the monitor device 112, or a wire for transmitting data to the monitor device, etc. For example, the connection may be a hard-wired communications connection such as, but not limited to, a universal serial bus (USB) cable, a FireWire cable, an Ethernet connection, or any other suitable wired communications connection. In some embodiments, the connection 110 may be wireless communications connection such as, but not limited to, a WiFi connection, a Bluetooth connection, a radio-frequency (RF) connection, a near-field communication (NFC) connection, a satellite connection, or any suitable wireless connection for transmitting data between the respiratory device 108 and the monitor device 112. For example, the respiratory device 108 may be capable of capturing raw data from the exhaled breath of the subject 102, as discussed in more detail below with reference to the monitor device 112, and transmitting that raw data to the monitor device 112 for analysis.

The monitor device 112 may be any device such as, but not limited to, a server, a desktop computer, a notebook, a laptop computer, a tablet computer, a handheld device, a smart-phone, a thin client, or any other electronic device or computing system capable of capable of storing, compiling, and organizing audio, visual, and/or textual data and receiving and sending that data to and from other computing devices, such as the IV drip 104, e.g., via the IV monitoring device 105, the respiratory device 108, the datastore 114, the display device 116, and/or the user devices 122A-C via one or more networks or connections, e.g., the network 118 and/or the network 120. For example, the monitor device 112 may be or may include, but is not limited to, an isotope ratio mass spectrometer system (IRMS), a vapor-phase isotope analyzer (e.g., by Picarro, Inc.; Sunnyvale, Calif.), a PCONE/Breathtek instruments (e.g., by Otsuka Pharmaceutical, Inc., Rockville, Md. & Japan), or a Gas Analyzing Thermopile Detection instruments (e.g., by Dexter Research, Dexter, Mich.), or any other known and suitable device, etc. In embodiments, the monitor device 112 may receive exhaled breath from the subject 102 captured by the respiratory device 108 and may measure the $^{13}CO_2$ to $^{12}CO_2$ ratio in the expired air, where the ratio correlates to a bloodstream level of lactic acid in the subject 102. The monitor device 112 may analyze the $^{13}CO_2$ to $^{12}CO_2$ ratio in the expired air from the subject and may determine a level of sepsis where a lower ratio of $^{13}CO_2$ to $^{12}CO_2$ indicates an increased level of sepsis. For example, after the subject 102 has been administered sodium bicarbonate with a carbon-13 isotope, a ratio of $^{13}CO_2$ to $^{12}CO_2$ may be continuously monitored, and a sepsis level may be determined by the monitor device 112. The monitor device 112 may store the measured $^{13}CO_2$ to $^{12}CO_2$ ratios and the corresponding determined sepsis level in the data store 114. The monitor device 112 may display an indication of the sepsis level on the display device 116 and/or output an alert based on the level of sepsis to another device, e.g., the display device 116 and/or the user device 122A-C. Further, it can be appreciated that the monitor device 112 may include one or more computing devices. For example, while the IV drip 104, the IV monitoring device 105, the respiratory device 108, the monitor device 112, the datastore 114, and the display device 116 are illustrated as separate devices, it can be appreciated that the IV drip 104, the IV monitoring device 105, the respiratory device 108, the monitor device 112, the datastore 114, and the display device 116 may be a single device or two or more devices comprising any combination of the IV drip 104, the IV monitoring device 105, the respiratory device 108, the monitor device 112, the datastore 114, and the display device 116. The monitor device may be implemented in a computer system such as the computer system 700 illustrated FIG. 7 using hardware, software executed on hardware, firmware, non-transitory computer readable media having instructions stored thereon, or a combination thereof and may be implemented in one or more computer systems or other processing systems. The monitor device 112 is discussed in more detail below with reference to FIG. 2.

The datastore 114 can be any suitable database configuration, such as a relational database, a structured query language (SQL) database, a distributed database, or an object database, etc. Suitable configurations and storage types will be apparent to persons having skill in the relevant. In one example of the environment 100, the datastore 114 may store data related to the subject 102, e.g., subject data 214 and/or carbon ratio data 216 as described in more detail below with reference to FIG. 2.

The display 116 can be any display capable of receiving display signals from another computing device, such as the IV drip 104, e.g., via the IV monitoring device 105, the respiratory device 108, the monitor device 112, the datastore 114, and/or the user devices 122A-C, and outputting those display signals to a display unit such as, but not limited to, a LCD screen, plasma screen, LED screen, DLP screen, CRT screen, etc. While the display 116 is illustrated as a separate device, it can be appreciated that the display device 116 may be a part of another device or combination of devices including, but not limited to, the IV monitoring device 105, the respiratory device 108, the monitor device 112, the datastore 114, and/or the user devices 122A-C.

The networks 118, 120 may be any networks suitable for performing the functions as disclosed herein and may include a local area network (LAN), a wide area network (WAN), a wireless network (e.g., WiFi), a mobile communication network, a satellite network, the Internet, fiber optic, coaxial cable, infrared, radio frequency (RF), or any combination thereof. Other suitable network types and configurations will be apparent to persons having skill in the relevant art. In general, the networks 118, 120 can be any combinations of connections and protocols that will support communications among the IV monitoring device 105, the respiratory device 108, the monitor device 112, the datastore 114, the display device 116, and/or the user devices 122A-C.

The user devices 122A-C may be any device such as, but not limited to, a server, a desktop computer, a notebook, a laptop computer, a tablet computer, a handheld device, a smart-phone, a thin client, or any other electronic device or computing system capable of capable of storing, compiling, and organizing audio, visual, and/or textual data and receiving and sending that data to and from other computing devices, such as the IV monitoring device 105, the respiratory device 108, the monitor device 112, the datastore 114, the display device 116, and/or the user devices 122A-C via one or more networks or connections, e.g., the network 118 and/or the network 120. For example, the user devices 122A-C may be a computing device used by a medical professional monitoring the status of the subject 102.

Monitor Device 112

Figure 2:
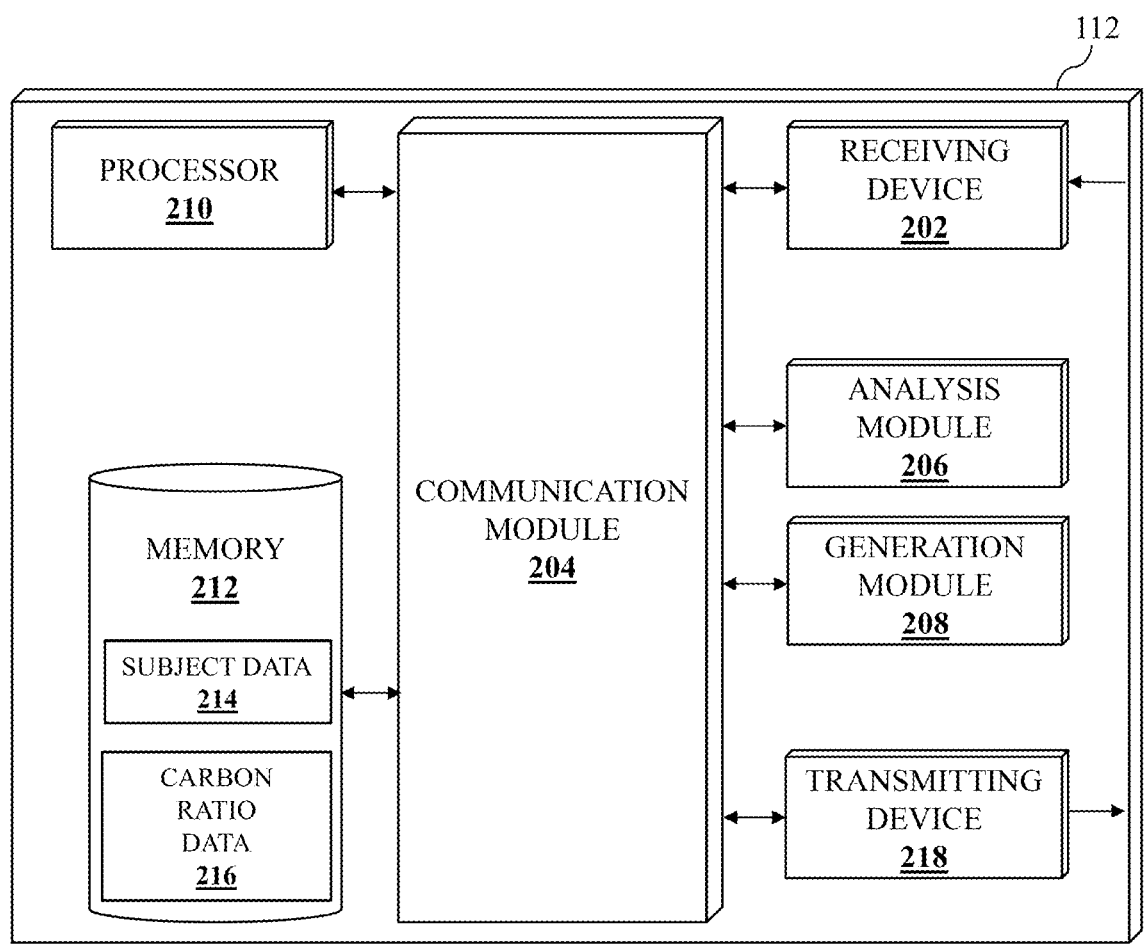
FIG. 2 is a block diagram illustrating the monitor device of FIG. 1 in accordance with aspects of the present disclosure.

FIG. 2 illustrates an example embodiment of a monitor device 112 in the environment 100. It will be apparent to persons having skill in the relevant art that the embodiment of the monitor device 112 illustrated in FIG. 2 is provided for illustration only and may not be exhaustive of all possible configurations of the monitor device 112 suitable for performing the functions as discussed herein. For example, the computer system 700 illustrated in FIG. 7 and discussed in more detail below may be a suitable configuration of the monitor device 112.

The monitor device 112 may include a receiving device 202. The receiving device 202 may be configured to receive data over one or more networks via one or more network protocols. In some instances, the receiving device 202 may be configured to receive data from the IV monitoring device 105, the respiratory device 108, the datastore 114, the display 116, the user devices 122A-C, and other systems and entities via one or more communication methods, such as radio frequency, local area networks, wireless area networks, cellular communication networks, Bluetooth, the Internet, etc. In some embodiments, the receiving device 202 may be comprised of multiple devices, such as different receiving devices for receiving data over different networks, such as a first receiving device for receiving data over a local area network and a second receiving device for receiving data via the Internet. The receiving device 202 may receive electronically transmitted data signals, where data may be superimposed or otherwise encoded on the data signal and decoded, parsed, read, or otherwise obtained via receipt of the data signal by the receiving device 202. In some instances, the receiving device 202 may include a parsing module for parsing the received data signal to obtain the data superimposed thereon. For example, the receiving device 202 may include a parser program configured to receive and transform the received data signal into usable input for the functions performed by the monitor device 112 to carry out the methods and systems described herein. The receiving device 202 may further be a communication receiver containing various components that may include, but which are not limited to, a demodulator, an amplifier, a frequency converter, a filter, an analog-to-digital converter, and/or buffer storage; receiving device 202 may further include multiple such receivers.

The receiving device 202 may be configured to receive data signals electronically transmitted by the respiratory device 108 that may be superimposed or otherwise encoded with data. For example, the monitor device 112 may receive data signals superimposed or otherwise encoded with exhaled breath data from the subject 102. The breath data received from the respiratory device 108 may include data regarding the carbon dioxide composition of the exhaled breath of the subject 102 including the levels of carbon-13 isotope and the levels of carbon-12 isotope levels. The monitor device 112 may receive data signals superimposed or otherwise encoded with IV data from the IV drip 104, e.g., via the IV monitoring device 105. For example, the IV data received from the IV drip 104, e.g., via the IV monitoring device 105, may include data regarding fluids being administered to the subject 102 such as, but not limited to, a composition of fluids being administered to the subject 102, amounts of fluids being administered to the subject 102, a rate of administration of fluids being administered to the subject 102, etc. The monitor device 112 may receive data signals superimposed or otherwise encoded with data from the datastore 114 such as the subject data 214 and/or the carbon ratio data 216, discussed in more detail below with reference to the datastore 114. In embodiments, the monitor device 112 may receive the exhaled breath from the subject 102 for direct analysis, which is discussed in more detail below with reference to the analysis module 206.

The monitor device 112 may also include a communication module 204. The communication module 204 may be configured to transmit data between/among modules, engines, databases, memories, and other components of the monitor device 112 for use in performing the functions discussed herein. The communication module 204 may be comprised of one or more communication types and utilize various communication methods for communications within a computing device. For example, the communication module 204 may be comprised of a bus, contact pin connectors, wires, etc. In some embodiments, the communication module 204 may also be configured to communicate between internal components of the monitor device 112 and external components of the monitor device 112, such as externally connected databases, display devices, input devices, etc. The monitor device 112 may also include a processing device 210, e.g., but not limited to, a microprocessor, computer, etc. The processing device 210 may be configured to perform the functions of the monitor device 112 discussed herein as will be apparent to persons having skill in the relevant art. In some embodiments, the processing device 210 may include and/or be comprised of a plurality of engines and/or modules specially configured to perform one or more functions of the processing device 210, receiving device 202, the analysis module 206, the generation module 208, the processor 210, the memory 212, and the transmitting device 218, etc. As used herein, the term "module" may be software or hardware particularly programmed to receive an input, perform one or more processes using the input, and provide an output. The input, output, and processes performed by various modules will be apparent to one skilled in the art based upon the present disclosure.

Figure 3:
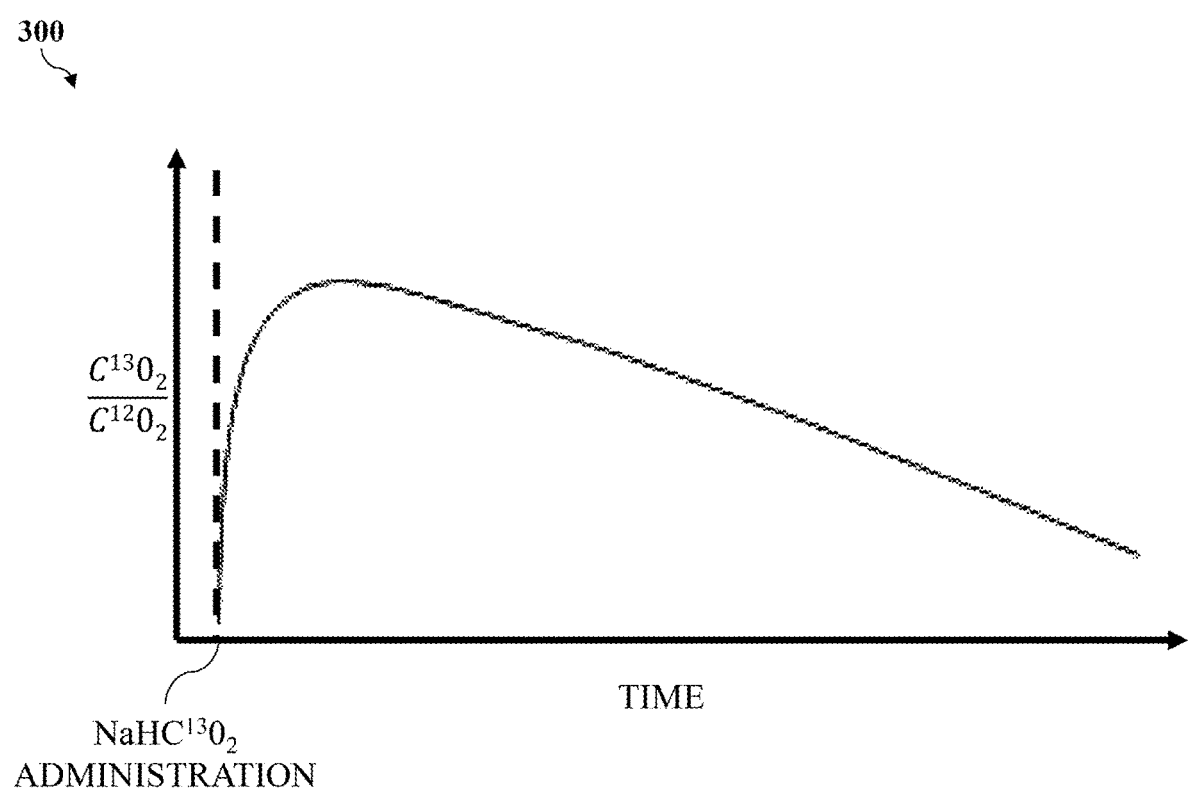
FIG. 3 is a graph illustrating the ratio of $^{13}CO_2/^{12}CO_2$ overtime in a subject injected one-time with a bicarbonate salt comprising a carbon-13 isotope in accordance with aspects of the present disclosure.
Figure 4:
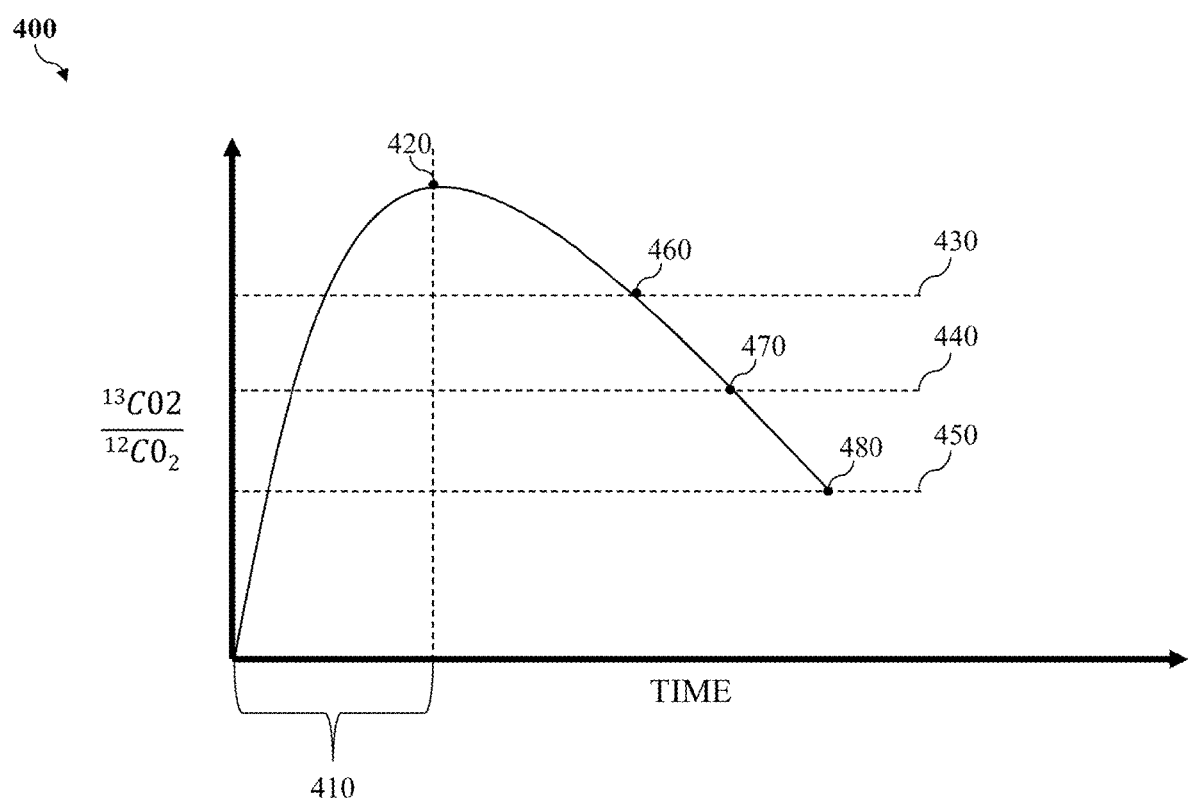
FIG. 4 is a graph illustrating the ratio of $^{13}CO_2/^{12}CO_2$ over-time in a subject continuously injected with a bicarbonate salt comprising a carbon-13 isotope in accordance with aspects of the present disclosure.

The monitor device 112 may include an analysis module 206. The analysis module 206 may be configured to analyze or otherwise process data for use by the monitor device 112 in performing the function discussed herein. The analysis module 206 may measure a ratio of carbon dioxide comprising a carbon-13 isotope ($^{13}CO_2$) to carbon dioxide comprising a carbon-12 isotope ($^{12}CO_2$) in the exhaled breath of the subject 102 after the subject has been administered the bicarbonate salt comprising a carbon-13 isotope, e.g., but not limited to, $NaH^{13}CO_3$. The analysis module 206 may analyze or otherwise process data received from the respiratory device 108, or the analysis module 206 may analyze or otherwise process the exhaled breath captured by the respiratory device 108. The analysis module 206 may measure the ratio of carbon dioxide comprising carbon-13 isotope ($^{13}CO_2$) to carbon dioxide comprising a carbon-12 isotope ($^{12}CO_2$) in the exhaled breath of the subject 102 continuously over a period of time, intermittently at defined time intervals, etc. For example, the monitor device 112 may measure the ratio of carbon dioxide comprising a carbon-13 isotope ($^{13}CO_2$) to carbon dioxide comprising a carbon-12 isotope ($^{12}CO_2$) in the exhaled breath of the subject 102 continuously during the subject's entire stay in the environment 100, every five minutes during the subject's entire stay in the environment 100, every half-hour during the subject's entire stay in the environment 100, every hour during the subject's entire stay in the environment 100, or any other suitable time interval; according to various aspects of the present disclosure, this may permit more frequent testing than ABG testing, which requires drawing blood and performing laboratory analysis (which may take at least 10-15 minutes once the blood reaches the laboratory) of the blood sample each time it is performed. As noted above, the analysis module 206 may analyze data received from the respiratory device 108 or the analysis module 206 may directly analyze the exhaled breath of the subject 102. In such embodiments where the analysis module 206 analyzes the exhaled breath of the subject 102 directs, the monitor device 112 may be and/or include elements of, but not limited to, an isotope ratio mass spectrometer system (IRMS), a vapor-phase isotope analyzer (e.g., by Picarro, Inc.; Sunnyvale, Calif.), a PCONE/Breathtek instruments (e.g., by Otsuka Pharmaceutical, Inc., Rockville, Md. & Japan), or a Gas Analyzing Thermopile Detection instruments (e.g., by Dexter Research, Dexter, Mich.), or any other known device capable of measuring the $^{13}CO_2$ to $^{12}CO_2$ ratio in the expired air. The analysis module 206 may determine a level of sepsis in the subject 102 based on the measure ratio of carbon dioxide comprising a carbon-13 isotope ($^{13}CO_2$) to carbon dioxide comprising a carbon-12 isotope ($^{12}CO_2$) in the exhaled breath of the subject 102. To determine a level of sepsis in the subject 102, the analysis module may compare the measured ratio of carbon dioxide comprising a carbon-13 isotope ($^{13}CO_2$) to carbon dioxide comprising a carbon-12 isotope ($^{12}CO_2$) in the exhaled breath of the subject 102 to a known threshold of carbon dioxide comprising a carbon-13 isotope ($^{13}CO_2$) to carbon dioxide comprising a carbon-12 isotope ($^{12}CO_2$) that indicates sepsis. For example, in humans, it is known that a bloodstream serum lactate levels greater than 4 mmol/l correlates to a 40% mortality rate while bloodstream serum lactate levels less than 2 mmol/l correlates to a mortality rate of less than 15%. Therefore, one or more pre-defined thresholds may be determined for different levels of sepsis. For example, a bloodstream serum lactate level of less than 2 mmol/l may indicate mild sepsis, 2-4 mmol/l may indicate moderate sepsis, and greater than 4 mmol/l may indicate severe sepsis. The bloodstream serum lactate level has a known correspondence to the ratio of carbon dioxide comprising carbon-13 isotope ($^{13}CO_2$) to carbon dioxide comprising a carbon-12 isotope ($^{12}CO_2$) in the exhaled breath of the subject 102. If the subject 102 is administered the $NaH^{13}CO_3$ or other bicarbonate salt prior to any onset of sepsis, the equilibration with the endogenous bicarbonate pools comprising a carbon-12 isotope in the subject 102 may be enabled. By equilibrating the carbon-13 and carbon-12 isotopes prior to sepsis onset, the $CO_2$ production that occurs as a result of lactate buffering may be distinguished from the $CO_2$ that may result from normal energy production. Consequently, the ratio of $^{13}CO_2$ to $^{12}CO_2$ may indicate a level of lactic acid production due to "abnormal" activity in the body and may be used to estimate a quantity of lactic acid, at least a relative quantity thereof, produced as a result of lactate buffering. This may be based on known relationships between lactic acid production and $CO_2$ production. When lactic acid begins to accumulate in the bloodstream, because the body of the subject 102 stores of bicarbonate now contain both $NaH^{13}CO_3$ and $NaH^{12}CO_3$ as a result of prior administration, both will be released into plasma and into exhaled breath of the subject 102 as $^{13}CO_2$ and $^{12}CO_2$. Thus, the amount of $^{13}CO_2$ in exhaled breath of the subject 102 will increase and will be indicated by a rise in the $^{13}CO_2/^{12}CO_2$ ratio. This marks the beginning of lactic acid accumulation, which may indicate the rise of sepsis in the subject 102. Referring to FIG. 3, the normal whole-body metabolism of a human subject, e.g., the subject 102, administered with a one-time dose of $NaH^{13}CO_3$ is illustrated as the ratio of $^{13}CO_2/^{12}CO_2$ in the exhaled breath of the human subject, e.g., the subject 102. Referring now to FIG. 4, a graph 400 illustrating the ratio of $^{13}CO_2/^{12}CO_2$ over time in a subject, e.g., the subject 102, continuously injected with $NaH^{13}CO_3$, e.g., via the IV drip 104 or other means, is illustrated. A base ratio 420 of $^{13}CO_2/^{12}CO_2$ in the exhaled breath of the subject 102 that is being continuously administered $NaH^{13}CO_3$ may be determined and continuously monitored. If NaH13CO or other bicarbonate salt has been administered prior to any onset of sepsis, a base ratio 420 of $^{13}CO_2/^{12}CO_2$ in the exhaled breath of the subject 102 may be established over an initial administration period 410 of $NaH^{13}CO_3$ to the subject 102. The graph 400 illustrates three pre-defined sepsis thresholds 430, 440, and 450. The pre-defined sepsis threshold 430 may be the lower limit of an indication of mild sepsis, e.g., a $^{13}CO_2/^{12}CO_2$ ratio in the exhaled breath of the subject 102 corresponding to a bloodstream lactate level of 1 mmol/l or any other pre-defined level, the pre-defined sepsis threshold 440 may be the lower limit of an indication of moderate sepsis, e.g., a $^{13}CO_2/^{12}CO_2$ ratio in the exhaled breath of the subject 102 corresponding to a bloodstream lactate level of 2 mmol/l or any other pre-defined level, and the pre-defined sepsis threshold 450 may be the lower limit of an indication of severe sepsis e.g., a $^{13}CO_2/^{12}CO_2$ ratio in the exhaled breath of the subject 102 corresponding to a bloodstream lactate level of 4 mmol/l or any other pre-defined level. As illustrated in FIG. 4, the subject 102 has a $^{13}CO_2/^{12}CO_2$ ratio in the exhaled breath that crosses into an indication of mild sepsis at time 460, a ratio of $^{13}CO_2/^{12}CO_2$ ratio in the exhaled breath that crosses into an indication of moderate sepsis at time 470, and. a ratio of $^{13}CO_2/^{12}CO_2$ ratio in the exhaled breath that crosses into an indication of severe sepsis at time 480. The progression through the different levels of sepsis from mild to severe indicate that the ratio of $^{13}CO_2/^{12}CO_2$ in the exhaled breath is decreasing as the subject 102 produces more $^{12}CO_2$ to buffer the sepsis that is occurring.

Referring back to FIG. 2, the monitor device 112 may include the generation module 208. The generation module 208 may be configured to generate data for use by the monitor device 112 in performing the functions discussed herein. The generation module 208 may receive instructions as input, e.g., from the analysis module 204, may generate data based on the instructions, and may output the generated data to one or more modules of the monitor device 112. In an embodiment, the generation module 208 may be configured to generate one or more sepsis level indications. The one or more sepsis level indications may be, but are not limited to, alerts, notifications, SMS messages, emails, optical outputs, audio outputs, or any other suitable indication, etc. The generation module 208 may generate an indication for display and/or output on one or more devices such as, but not limited to, the display device 116, and the user devices 122A-C, etc. For example, the generation module 208 may generate an alert or notification of a sepsis level of the subject 102 for output to the display device 116. The alert or notification for output to the display device 116 may be a textual alert of the sepsis level, an audio alert, e.g., a warning sound, an optical alert, e.g., a flashing light, etc. As another example, the indication may be an audio and/or visual alert for output to a remote display, e.g., the user device 122A, a text message for output to a mobile device, e.g., the user device 122B, and email for output to a computer, e.g., the user device 122C, etc. While several examples of sepsis level indications are described, it can be appreciated that any suitable alert or notification capable of being output or otherwise displayed to one or more persons may be generated by the generation module 208 to indicate a level of sepsis in the subject 102. The generation module 208 may generate instructions or recommendations for treating the subject 102 based on the determined level of sepsis in the subject 102. For example, the generation module 208 may generate a recommended care plan for the subject 102 based on the level of sepsis. The care plan may be include one or more medical intervention recommendations such as, but not limited to, the administration of antibiotics, e.g., via the IV drip 104, the administration of other fluids and/or nutrients, e.g., via the IV drip 104, administration of oxygen, e.g., via the respiratory device 108, dialysis, surgery, etc. The generation module may be pre-programmed to generate instructions to one or more devices such as the IV monitoring device 105, the respiratory device 108, the display 116, the user devices 122A-C, or any other suitable device for carrying out the recommended care plan. For example, the generation module 208 may generate instructions to the IV monitoring device 105, e.g., beginning administration of a fluid and/or adjusting a level of fluid being administered to the subject 102, the respiratory device 108, e.g., increasing a level of oxygen being administered to the subject 102, the display 116, and/or one or more of the user devices 122A-C, etc. for treating the subject 102 in response to the sepsis level determination. The generation module 208 may generate a textual care plan, e.g., a physical document, a digital document, a PDF file, an e-mail, a text message, etc. For example, the generation module 208 may generate an e-mail with a detailed care plan for implementation by a medical professional.

The monitor device 112 may also include a memory 212. The memory 212 may be configured to store data for use by the monitor device 112 in performing the functions discussed herein, such storing data. The memory 212 may be configured to store data using suitable data formatting methods and schema and may be any suitable type of memory, such as read-only memory, random access memory, etc. The memory 212 may include, for example, communication protocols and standards, data formatting standards and protocols, program code for modules and application programs of the processing device, and other data that may be suitable for use by the monitor device 112 in the performance of the functions disclosed herein as will be apparent to persons having skill in the relevant art. In some embodiments, the memory 212 may be comprised of or may otherwise include a relational database that utilizes structured query language for the storage, identification, modifying, updating, accessing, etc. of structured data sets stored therein. In embodiments, the memory 212 may include subject data 214 and/or carbon ratio data 216. The subject data 216 may include any data related to the subject 102 such as, but is not limited to, subject identification, subject type, subject name, subject medical information, subject vital information, etc. The carbon ratio data 216 may include the measured $^{13}CO_2/^{12}CO_2$ ratio in the exhaled breath of the subject 102. For example, the monitor device 112 may store the continuously measured $^{13}CO_2/^{12}CO_2$ ratio in the exhaled breath of the subject 102 for charting or other analysis, e.g., the graph 400 illustrated in FIG. 4. The carbon ratio data 216 may be included in the subject data 214, e.g., stored in a file corresponding to the subject 102.

The monitor device 112 may also include a transmitting device 218. The transmitting device 218 may be configured to transmit data over one or more networks via one or more network protocols. In some instances, the transmitting device 218 may be configured to transmit data to the IV drip 104, e.g., via the IV monitoring device 105, the respiratory device 108, the datastore 114, the display device 116, the user devices 122A-C, and other entities via one or more communication methods, local area networks, wireless area networks, cellular communication, Bluetooth, radio frequency, the Internet, etc. In some embodiments, the transmitting device 218 may be comprised of multiple devices, such as different transmitting devices for transmitting data over different networks, such as a first transmitting device for transmitting data over a local area network, e.g., the network 118, and a second transmitting device for transmitting data via the Internet, e.g., the network 120. The transmitting device 218 may electronically transmit data signals that have data superimposed that may be parsed by a receiving device. In some instances, the transmitting device 218 may include one or more modules for superimposing, encoding, or otherwise formatting data into data signals suitable for transmission. The transmitting device may thus comprise one or more transmitters, of which each transmitter may include, for example, a modulator, a frequency converter, a filter, a buffer, a digital-to-analog converter, etc., but is not limited to including any or all of these components.

The transmitting device 218 may be configured to electronically transmit data signals to one or more of the IV drip 104, e.g., via the IV monitoring device 105, the respiratory device 108, the display 116, and/or the user devices 122A-C, which may be superimposed or otherwise encoded with instructions related to a computer executable command generated by the monitor device 112, e.g., via the generation module 208. For example, the transmitting device 220 may transmit the sepsis level indication to the display device 116 and/or to one or more of the user devices 122A-C. Further, the transmitting device 220 may transmit the generated instructions or recommendations, e.g., a care plan, for treating the subject 102 based on the determined level of sepsis in the subject 102 to the IV drip 104, e.g., via the monitoring device 105, the respiratory device 108, the display device 116, and/or to one or more of the user devices 122A-C. For example, the transmitting device 220 may transmit instructions to the IV monitoring device 105 to begin and/or adjust the administration of antibiotics to the subject 102, e.g., via the IV drip 104. As another example, the transmitting device 220 may transmit a textual care plan, e.g., an email, to a medical profession, e.g., via the user device 122C.

Process for Monitoring Sepsis in a Subject

Figure 5A:
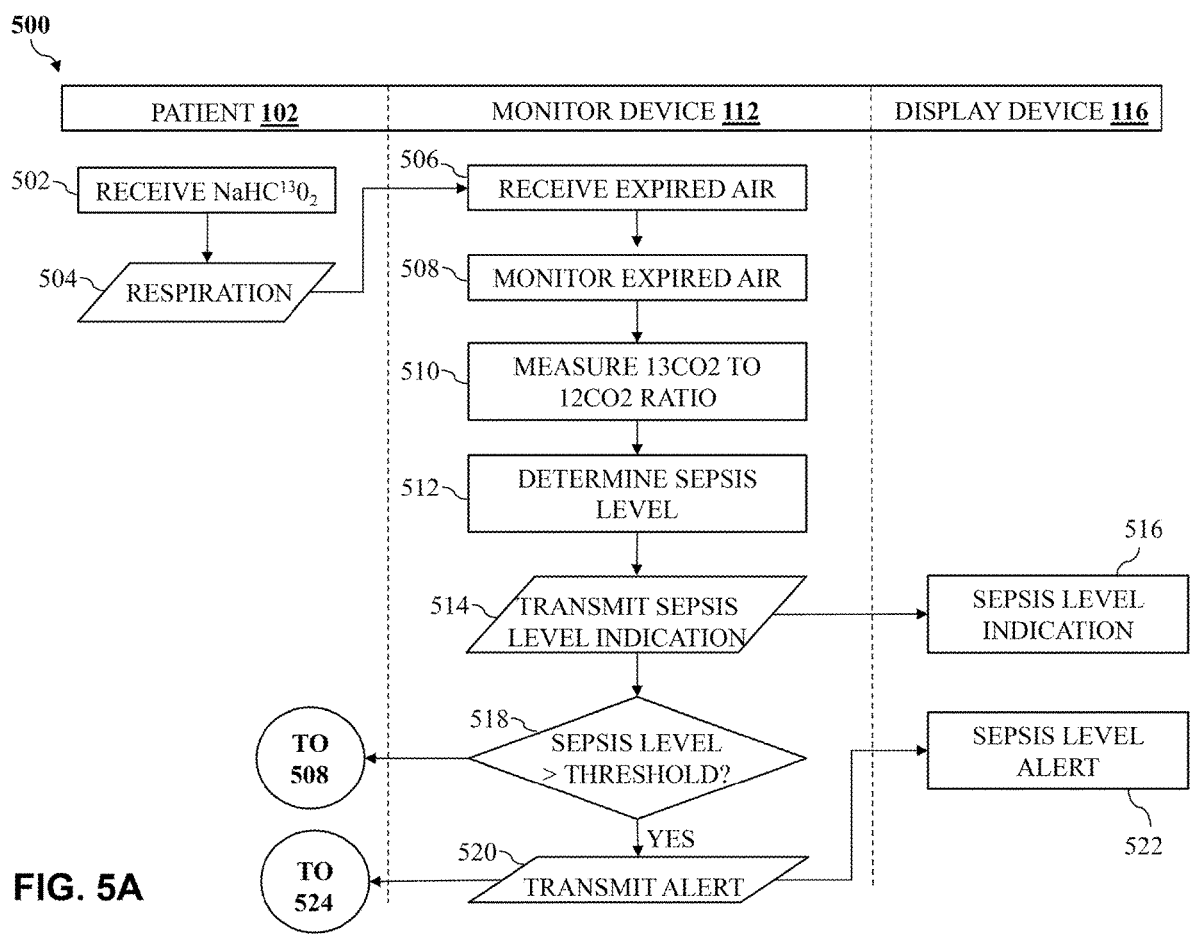
FIGS. 5A-B are a flow diagram illustrating a process for monitoring sepsis in a subject in accordance with aspects of the present disclosure.
Figure 5B:
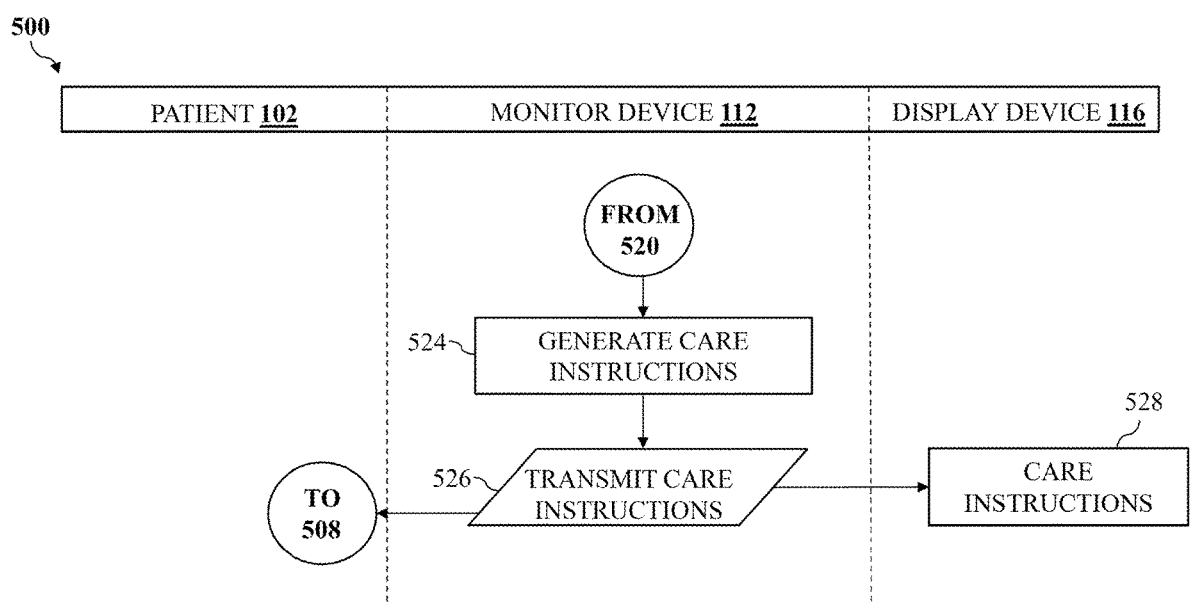

FIGS. 5A-B illustrate a process 500 for monitoring sepsis in a subject in accordance with exemplary embodiments.

In the block 502, the subject 102 may be administered a bicarbonate salt comprising a carbon-13 isotope. In various embodiments the bicarbonate salt may be sodium bicarbonate, but any suitable bicarbonate salt may be used. The bicarbonate salt comprising a carbon-13 isotope may be administered to the subject 102 via an IV drip, e.g., the IV drip 104, and may be administered on a continuous basis to allow continuous monitoring of the subject 102. However, it can be appreciated that the subject 102 may be administered the bicarbonate salt comprising a carbon-13 isotope at any suitable time interval using any suitable method of administration as discussed in more detail above with reference to FIG. 1.

In the block 504, the exhaled breath of the subject 102 may be captured, e.g., via the respiratory device 108. The exhaled breath of the subject 102 may be transmitted to the monitor device 112, or data generated by the respiratory device 108 and representing the exhaled breath of the subject 102 may be transmitted to the monitor device 112, depending on the configuration of the respiratory device 108 and the monitor device 112 as discussed in more detail above with reference to FIGS. 1-2.

In the block 506, the monitor device 112 may receive the exhaled breath of the subject 102 (or data representing the exhaled breath of the subject 102) and may monitor the exhaled breath of the subject 102 in the block 508. The monitoring of the exhaled breath of the subject 102 may be continuous or intermittent such as, but not limited to, defined time intervals, e.g., every minute, every 5 minutes, every half-hour, every hour, etc.

In the block 510, the monitor device 112 may measure a ratio of carbon dioxide comprising the carbon-13 isotope ($^{13}CO_2$) to carbon dioxide comprising a carbon-12 isotope ($^{12}CO_2$) in the monitored expired air. The ratio of carbon dioxide containing the carbon-13 isotope ($^{13}CO_2$) to carbon dioxide comprising a carbon-12 isotope ($^{12}CO_2$) in the monitored expired air correlates to a bloodstream level of lactic acid in the subject 102, as explained above. The monitor device 112 may store the measurements for analysis, e.g., in the datastore 114.

In the block 512, the monitor device 112 may determine a level of sepsis in the subject 102 based on the measure ratio of carbon dioxide containing the carbon-13 isotope ($^{13}CO_2$) to carbon dioxide comprising a carbon-12 isotope ($^{12}CO_2$) in the monitored expired air. For example, the monitor device 112 may compare the measured ratio, or a serum lactate value corresponding to the measured ratio, to known ratios or known thresholds that indicate a particular level of sepsis in the subject 102, e.g., no sepsis, mild sepsis, moderate sepsis, or severe sepsis, etc.

In the block 514, the monitor device may transmit an indication of the level of sepsis to another device such as, but not limited to, the display device 116 and/or the user device 122A-C, which may receive the indication at the block 516. The indication may be, but is not limited to, a textual output, an audio output, an optical output, or any other suitable output for display or other output by another device, e.g., the display device 116 and/or the user devices 122A-C. For example, the indication may be a text display showing the level of sepsis, e.g., "MILD SEPSIS DETECTED," or an audio output, e.g., an alarm sound associated with a level of sepsis, or an optical output, e.g., a flashing light associated with a level of sepsis, etc. Further, the indication may include the measured ratio and/or a graph of the measured ratio over time, e.g., the graph 400 as illustrated in FIG. 4. Furthermore, or additionally, the indication may include a serum lactate level corresponding to the measured ratio and/or a graph of the serum lactate level over time.

In the block 518, the monitor device may determine if the determined level of sepsis is above one or more thresholds. If the determined level of sepsis is above a certain threshold, discussed in more detail above with reference to FIG. 2, the monitor device 112 may generate and transmit, at block 520, an alert for transmission to one or more devices, e.g., the display device 116 and/or the user device 122A-C, which receives the alert at block 522. If the determined level of sepsis is not above any threshold, then the monitor device 112 may continue to monitor the exhaled breath of the subject 102.

From the block 520, the process 500 may proceed to the block 524. In the block 524, the monitor device 112, may generate instructions and/or recommendations, e.g., a care plan, for treating the subject 102 based on the determined level of sepsis as discussed in more detail above with reference to FIG. 2. The monitor device 112 may transmit the generated instructions and/or recommendations to another computing device, e.g., the IV monitor device 105, the respiratory device 108, the display 116, and/or the user device 122A-C, etc., at the block 526. At the block 528, another device, e.g., one of the IV monitor device 105, the respiratory device 108, the display 116, and/or the user device 122A-C, etc. may receive the generated instructions and/or recommendations and, if enabled to, may implement the instructions. For example, if the generated instructions include an instruction to the IV monitoring device 105 to administer a certain dosage of antibiotics to the subject 102, the IV monitoring device may begin the administration of antibiotics, e.g., via the IV drip 104, to the subject 102.

While the process 500 is illustrated and described in a series of numbered blocks, it can be appreciated that in some embodiments one or more blocks may be omitted or and/or the order of blocks may be rearranged without departing from the spirit of the disclosed subject matter.

Example Method for Monitoring Sepsis in a Subject

Figure 6:
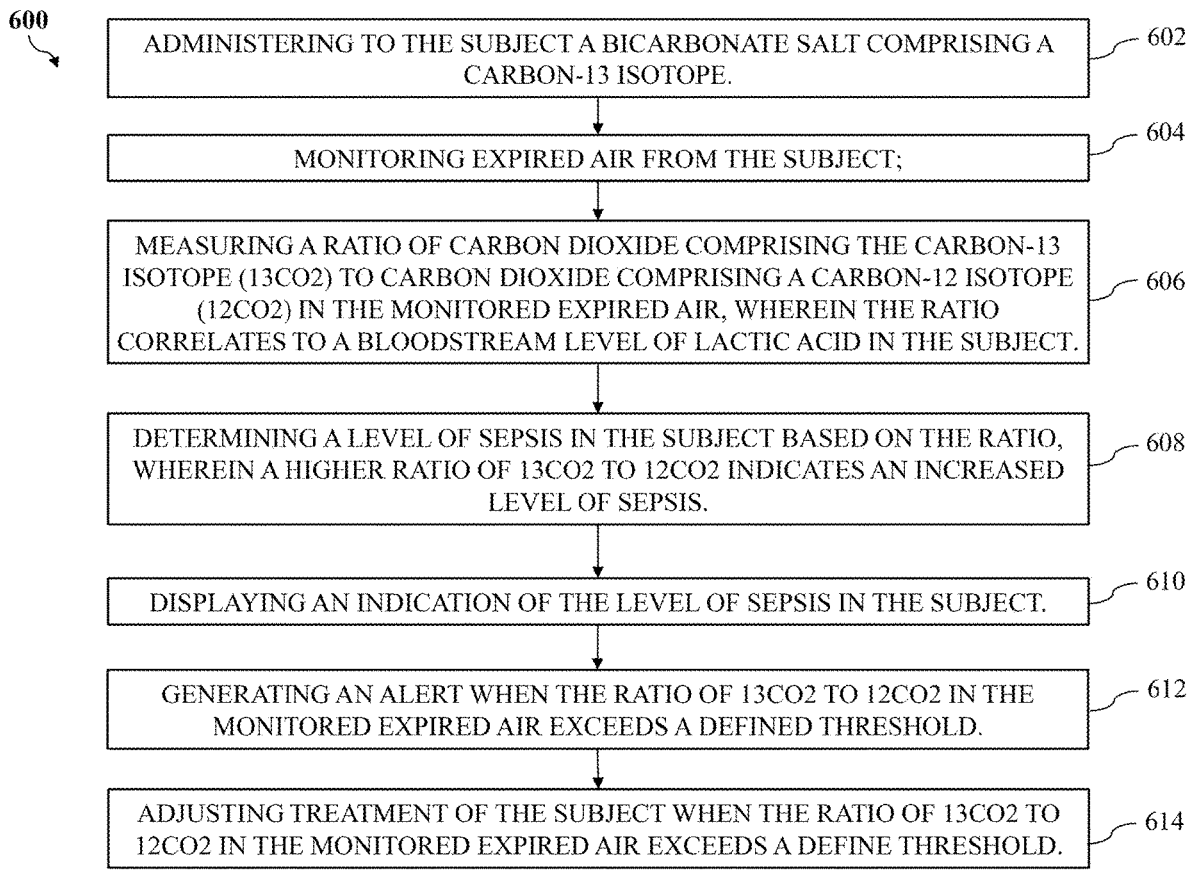
FIG. 6 is a flow diagram illustrating an exemplary method for monitoring sepsis in a subject in accordance with aspects of the present disclosure.

FIG. 6 illustrates a flow chart of an example of a method 600 for generating graphics for monitoring sepsis in a subject in accordance with aspects of the present disclosure.

In block 602, the subject 102 may be administered, e.g., via the IV drip 104, a bicarbonate salt comprising a carbon-13 isotope. In embodiments the bicarbonate salt may be sodium bicarbonate, but any suitable bicarbonate salt may be used. The bicarbonate salt comprising a carbon-13 isotope may be administered to the subject 102 via an IV drip, e.g., the IV drip 104, and may be administered on a continuous basis to allow continuous monitoring of the subject 102. However, it can be appreciated that the subject 102 may be administered the bicarbonate salt comprising a carbon-13 isotope at any suitable time interval using any suitable method of administration, e.g., orally, as discussed in more detail above with reference to FIG. 1.

In block 604, the monitor device 112 may monitor the expired breath of the subject 102. For example, the monitor device 112 may receive, e.g., via the receiving device 202, the exhaled breath of the subject 102 from a device, e.g., the respiratory device 108, capable of capturing the respiration of the subject 102; according to another aspect of the disclosure, the monitor device 112 may receive from the respiratory device 108 data reflecting the exhaled breath of the subject 102. The monitor device 112 may monitor the exhaled breath of the subject 102 continuously or intermittently such as, but not limited to, defined time intervals, e.g., every minute, every 5 minutes, every half-hour, every hour, etc.

In block 606, the monitor device 112 may measure, e.g., via the analysis module 206, a ratio of carbon dioxide comprising the carbon-13 isotope ($^{13}CO_2$) to carbon dioxide comprising a carbon-12 isotope ($^{12}CO_2$) in the monitored expired air. The ratio of carbon dioxide comprising the carbon-13 isotope ($^{13}CO_2$) to carbon dioxide comprising a carbon-12 isotope ($^{12}CO_2$) in the monitored expired air correlates to a bloodstream level of lactic acid in the subject.

In block 608, the monitor device 112 may determine, e.g., via the analysis module 206, a level of sepsis in the subject based on the ratio, where a lower ratio of $^{13}CO_2$ to $^{12}CO_2$ indicates an increased level of sepsis.

In block 610, the monitor device 112 may generate and display, e.g., via the generation module 208, an indication of the level of sepsis in the subject. The monitor device may display, e.g., transmit via the transmitting device 218, the indication of the level of sepsis to one or more devices such as, but not limited to, the display device 116, one or more of the user devices 122A-C, etc.

In block 612, the monitor device may generate, e.g., via the generation module 208, an alert when the ratio of $^{13}CO_2$ to $^{12}CO_2$ in the monitored expired air exceeds a defined threshold. The monitor device may transmit, e.g. via the transmitting device 218, the alert to one or more devices such as, but not limited to, the display device 116, one or more of the user devices 122A-C, etc.

In block 614, the monitor device 112 may adjust treatment of the subject 102 when the ratio of $^{13}CO_2$ to $^{12}CO_2$ in the monitored expired air exceeds a define threshold. For example, the monitor device may generate, e.g., via the generation module 208, instructions and/or recommendations for medical care for the subject 102 and may transmit, e.g., via the transmitting device 218, the instructions and/or recommendations to one or more devices such as, but not limited to, the IV drip 104, e.g., via the IV monitoring device 105, the respiratory device 108, the display 116, one or more of the user devices 122A-C, etc. The one or more devices, e.g., the IV drip 104 (e.g., via the IV monitoring device 105), the respiratory device 108, the display 116, one or more of the user devices 122A-C, etc. may execute the received instructions and/or recommendations. For example, if the generated instructions include an instruction to the IV monitoring device 105 to administer a certain dosage of antibiotics to the subject 102, the IV monitoring device may begin the administration of antibiotics, e.g., via the IV drip 104, to the subject 102.

Computer System Architecture

Figure 7:
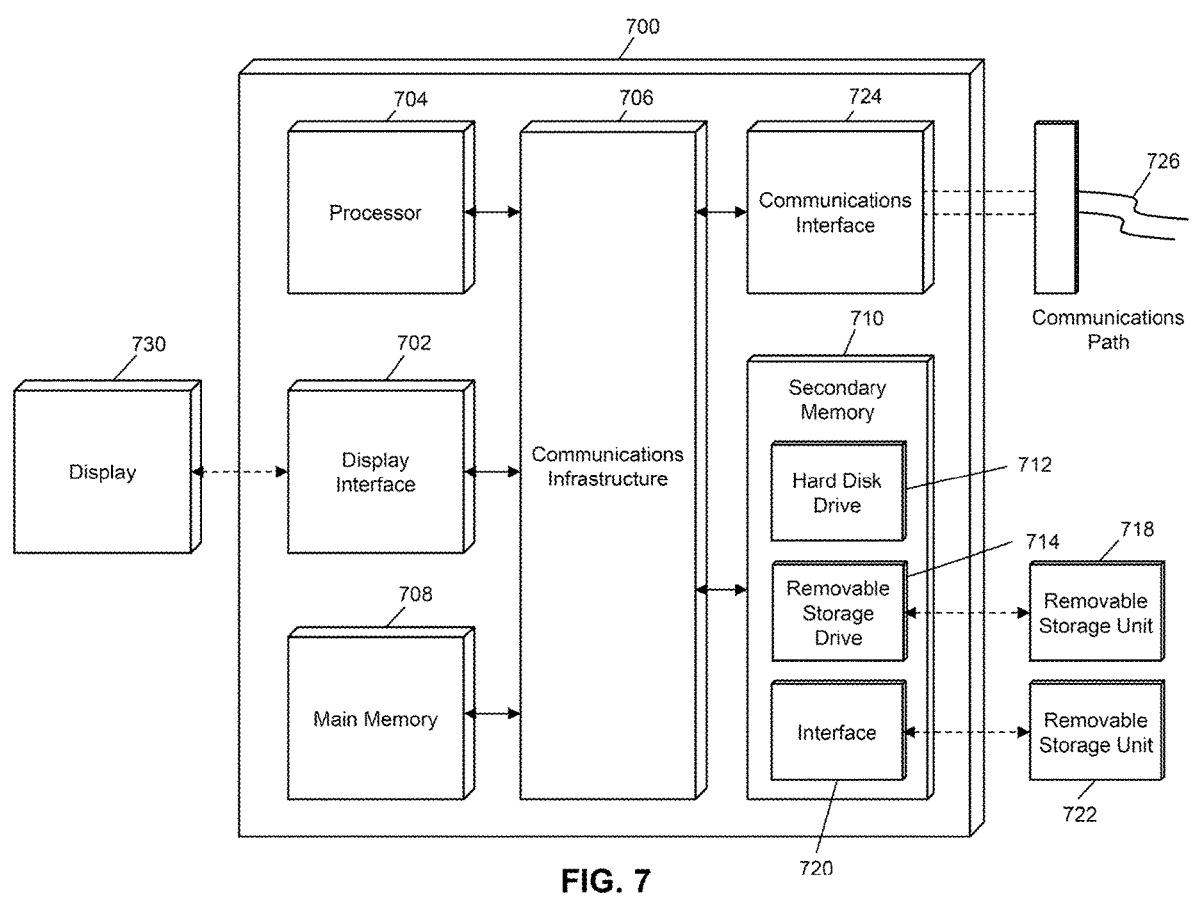
FIG. 7 is a block diagram illustrating a computer system architecture in accordance with aspects of the present disclosure.

FIG. 7 illustrates a computer system 700 in which embodiments of the present disclosure, or portions thereof, may be implemented. For example, the IV monitoring device 105, the respiratory device 108, the monitor device 112, the datastore 114, the display device 116, and the user devices 122A-C, may be implemented in the computer system 700 using hardware, software executed on hardware, firmware, non-transitory computer readable media having instructions stored thereon, or a combination thereof and may be implemented in one or more computer systems or other processing systems. Hardware, software, or any combination thereof may embody modules and components used to implement the processes and methods of FIGS. 5A-B and 6.

If programmable logic is used, such logic may execute on a commercially available processing platform configured by executable software code to become a specific purpose computer or a special-purpose device (e.g., programmable logic array, application-specific integrated circuit, etc.). A person having ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, at least one processor device and a memory may be used to implement the above-described embodiments.

A processor unit or device as discussed herein may be a single processor, a plurality of processors, or combinations thereof. Processor devices may have one or more processor "cores." The terms "computer program medium," "non-transitory computer readable medium," and "computer usable medium" as discussed herein are used to generally refer to tangible media such as, but not limited to, a removable storage unit 718, a removable storage unit 722, and a hard disk installed in hard disk drive 712.

Various embodiments of the present disclosure are described in terms of this example computer system 700. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single- or multi-processor machines. In addition, in some embodiments the order of operations may be rearranged without departing from the spirit of the disclosed subject matter.

Processor device 704 may be a special-purpose or a general-purpose processor device specifically configured to perform the functions discussed herein. The processor device 704 may be connected to a communications infrastructure 706, such as a bus, message queue, network, multi-core message-passing scheme, etc. The network may be any network suitable for performing the functions as disclosed herein and may include a local area network (LAN), a wide area network (WAN), a wireless network (e.g., but not limited to, WiFi), a mobile communication network, a satellite network, the Internet, fiber optic, coaxial cable, infrared, radio frequency (RF), or any combination thereof. Other suitable network types and configurations will be apparent to persons having skill in the relevant art. The computer system 700 may also include a main memory 708 (e.g., random access memory, read-only memory, etc.), and may also include a secondary memory 710. The secondary memory 710 may include a hard disk drive 712 and a removable storage drive 714, such as a floppy disk drive, a magnetic tape drive, an optical disk drive, a flash memory, etc.

The removable storage drive 714 may read from and/or write to the removable storage unit 718 in a well-known manner. The removable storage unit 718 may include one or more removable storage media that may be read by and written to the removable storage drive 714. For example, if the removable storage drive 714 is a floppy disk drive or universal serial bus port, the removable storage unit 718 may be a floppy disk or portable flash drive, respectively. In one embodiment, the removable storage unit 718 may be a non-transitory computer readable recording medium.

In some embodiments, the secondary memory 710 may include alternative means for allowing computer programs or other instructions to be loaded into the computer system 700, for example, the removable storage unit 722 and an interface 720. Examples of such means may include a program cartridge and cartridge interface (e.g., as found in video game systems), a removable memory chip (e.g., EEPROM, PROM, etc.) and associated socket, and other removable storage units 722 and interfaces 720 as will be apparent to persons having skill in the relevant art.

Data stored in the computer system 700 (e.g., in the main memory 708 and/or the secondary memory 710) may be stored on any type of suitable computer readable media, such as optical storage (e.g., a compact disc, digital versatile disc, Blu-ray disc, etc.) or magnetic tape storage (e.g., a hard disk drive). The data may be configured in any type of suitable database configuration, such as a relational database, a structured query language (SQL) database, a distributed database, an object database, graphs, charts, etc. Suitable configurations and storage types will be apparent to persons having skill in the relevant art.

The computer system 700 may also include a communications interface 724. The communications interface 724 may be configured to allow software and data to be transferred between the computer system 700 and external devices. Exemplary communications interfaces 724 may include a modem, a network interface (e.g., an Ethernet card), a communications port, a PCMCIA slot and card, etc. Software and data transferred via the communications interface 724 may be in the form of signals, which may be electronic, electromagnetic, optical, or other signals as will be apparent to persons having skill in the relevant art. The signals may travel via a communications path 726, which may be configured to carry the signals and may be implemented using wire, cable, fiber optics, a phone line, a cellular phone link, a radio frequency link, etc.

The computer system 700 may further include a display interface 702. The display interface 702 may be configured to allow data to be transferred between the computer system 700 and external display 730. Exemplary display interfaces 702 may include high-definition multimedia interface (HDMI), digital visual interface (DVI), video graphics array (VGA), etc. The display 730 may be any suitable type of display for displaying data transmitted via the display interface 702 of the computer system 700, including a cathode ray tube (CRT) display, liquid crystal display (LCD), light-emitting diode (LED) display, capacitive touch display, thin-film transistor (TFT) display, etc.

Computer program medium and computer usable medium may refer to memories, such as the main memory 708 and secondary memory 710, which may be memory semiconductors (e.g., DRAMs, etc.). These computer program products may be means for providing software to the computer system 700. Computer programs (e.g., computer control logic) may be stored in the main memory 708 and/or the secondary memory 710. Computer programs may also be received via the communications interface 724. Such computer programs, when executed, may enable computer system 700 to implement the present methods as discussed herein. In particular, the computer programs, when executed, may enable processor device 704 to implement the processes and methods illustrated by FIGS. 5A-B and 6, as discussed herein. Accordingly, such computer programs may represent controllers of the computer system 700. Where the present disclosure is implemented using software, the software may, for example, be stored in a computer program product and loaded into the computer system 700 using the removable storage drive 714, interface 720, and hard disk drive 712, or communications interface 724.

The processor device 704 may comprise one or more modules or engines configured to perform the functions of the computer system 700. Each of the modules or engines may be implemented using hardware and, in some instances, may also utilize software, such as corresponding to program code and/or programs stored in the main memory 708 or secondary memory 710. In such instances, program code may be compiled by the processor device 704 (e.g., by a compiling module or engine) prior to execution by the hardware of the computer system 700. For example, the program code may be source code written in a programming language that is translated into a lower-level language, such as assembly language or machine code, for execution by the processor device 704 and/or any additional hardware components of the computer system 700. The process of compiling may include the use of lexical analysis, preprocessing, parsing, semantic analysis, syntax-directed translation, code generation, code optimization, and any other techniques that may be suitable for translation of program code into a lower-level language suitable for controlling the computer system 700 to perform the functions disclosed herein. It will be apparent to persons having skill in the relevant art that such processes result in the computer system 700 being a specially configured computer system 700 uniquely programmed to perform the functions discussed above.

Techniques consistent with the present disclosure may provide, among other features, systems and methods for monitoring sepsis in a subject. While various exemplary embodiments of the disclosed system and method have been described above it should be understood that they have been presented for purposes of example only, not limitations. Such examples are not exhaustive and do not limit the disclosure to the precise form(s) disclosed. Modifications and variations are possible in light of the above teachings or may be acquired from practicing of the disclosure, without departing from the breadth or scope.

What is claimed is:

1. A method of monitoring sepsis in a subject, the method comprising:
    monitoring expired air from the subject, wherein the subject has been administered a bicarbonate salt comprising a carbon-13 isotope;
    measuring a ratio of carbon dioxide comprising the carbon-13 isotope ($^{13}CO_2$) to carbon dioxide comprising a carbon-12 isotope ($^{12}CO_2$) in the monitored expired air, wherein the ratio correlates to a bloodstream level of lactic acid in the subject;
    determining a level of sepsis in the subject based on the ratio, wherein a lower ratio of $^{13}CO_2$ to $^{12}CO_2$ indicates an increased level of sepsis; and
    displaying an indication of the level of sepsis in the subject.

2. The method of claim 1, further comprising:
    generating an alert when the ratio of $^{13}CO_2$ to $^{12}CO_2$ in the monitored expired air exceeds a defined threshold.

3. The method of claim 1, further comprising:
    translating the measured ratio of $^{13}CO_2$ to $^{12}CO_2$ in the monitored expired air to a serum lactate level on the bloodstream of the subject.

4. The method of claim 1, further comprising:
    adjusting treatment of the subject when the ratio of $^{13}CO_2$ to $^{12}CO_2$ in the monitored expired air exceeds a defined threshold, wherein the adjusting the treatment of the subject includes:
    generating a care plan for the subject based on the determined level of sepsis, the care plan including instructions for treating the subject; and
    transmitting the care plan to one or more external devices.

5. The method of claim 1, wherein the monitoring the expired air from the subject is performed continuously or intermittently.

6. The method of claim 1, wherein the bicarbonate salt comprising the carbon-13 isotope is administered to the subject via one or more of: an intravenous fluid drip, orally, or injection.

7. The method of claim 1, wherein the bicarbonate salt comprising the carbon-13 isotope is administered orally to the subject.

8. The method of claim 1, wherein the monitoring the expired air from the subject includes:
capturing exhaled breath of the subject via a device capable of measuring the $^{13}CO_2$ to $^{12}CO_2$ ratio in the expired air.

9. The method of claim 1, wherein the bicarbonate salt is sodium bicarbonate ($NaHCO_3$).

10. A device, the device comprising:
a respiratory monitor configured to monitor expired air from a subject, wherein the subject has been administered a bicarbonate salt comprising a carbon-13 isotope;
a processor configured to:
measure a ratio of carbon dioxide comprising the carbon-13 isotope ($^{13}CO_2$) to a carbon dioxide comprising a carbon-12 isotope ($^{12}CO_2$) in the monitored expired air, wherein the ratio correlates to a bloodstream level of lactic acid in the subject; and
determine a level of sepsis in the subject based on the ratio, wherein a lower ratio of $^{13}CO_2$ to $^{12}CO_2$ indicates an increased level of sepsis; and
a display configured to display an indication of the level of sepsis in the subject.

11. The device of claim 10, wherein the processor is further configured to:
generate an alert when the ratio of $^{13}CO_2$ to $^{12}CO_2$ in the expired air exceeds a defined threshold.

12. The device of claim 10, wherein the respiratory monitor is configured to continuously monitor expired air from the subject.

13. The device of claim 10, wherein the processor is further configured to:
translate the measured ratio of $^{13}CO_2$ to $^{12}CO_2$ in the monitored expired air to a serum lactate level on the bloodstream of the subject.

14. The device of claim 10, wherein the respiratory monitor is configured to capture exhaled breath of the subject via a device capable of measuring the $^{13}CO_2$ to $^{12}CO_2$ ratio in the expired air.

15. A non-transitory computer program product for monitoring sepsis in a subject, the computer program product comprising:
a computer-readable storage medium having program instructions embodied therewith, the program instructions executable by a computer to cause the computer to perform a method, comprising:
receiving a carbon-13 isotope ($^{13}CO_2$) measurement and a carbon-12 isotope ($^{12}CO_2$) measurement in expired air from a subject, wherein the subject has been administered a bicarbonate salt comprising the carbon-13 isotope;
determining a ratio of $^{13}CO_2$ to $^{12}CO_2$ based on the $^{13}CO_2$ measurement and the $^{12}CO_2$ measurement, wherein the ratio correlates to a bloodstream level of lactic acid in the subject;
determining a level of sepsis in the subject based on the ratio, wherein a lower ratio of $^{13}CO_2$ to $^{12}CO_2$ indicates an increased level of sepsis; and
displaying an indication of the level of sepsis in the subject.

16. The computer program product of claim 15, the method further comprising:
generating an alert when the ratio of $^{13}CO_2$ to $^{12}CO_2$ in the monitored expired air exceeds a defined threshold.

17. The computer program product of claim 15, wherein the $^{13}CO_2$ measurement and the $^{12}CO_2$ measurement are received continuously.

* * * * *